(12) United States Patent
Ahluwalia et al.

(10) Patent No.: US 9,243,220 B2
(45) Date of Patent: Jan. 26, 2016

(54) BIOREACTOR CHAMBER

(75) Inventors: Arti Ahluwalia, Massa (IT); Daniele Mazzei, Pisa (IT); Bruna Vinci, Serra San Bruno (IT); Giovanni Vozzi, Pisa (IT)

(73) Assignee: Kirkstall Limited, Sheffield, South Yorkshire (GB)

( * ) Notice: Subject to any disclaimer, the term of this patent is extended or adjusted under 35 U.S.C. 154(b) by 744 days.

(21) Appl. No.: 13/057,083

(22) PCT Filed: Jul. 31, 2009

(86) PCT No.: PCT/GB2009/050965
§ 371 (c)(1),
(2), (4) Date: Feb. 1, 2011

(87) PCT Pub. No.: WO2010/013069
PCT Pub. Date: Feb. 4, 2010

(65) Prior Publication Data
US 2011/0129911 A1    Jun. 2, 2011

(30) Foreign Application Priority Data

Aug. 1, 2008  (GB) .................... 0814033.7
Aug. 1, 2008  (GB) .................... 0814034.5
May 15, 2009  (GB) .................... 0908400.5
May 15, 2009  (GB) .................... 0908404.7

(51) Int. Cl.
*C12M 1/00* (2006.01)
*C12M 3/00* (2006.01)
*B01J 19/00* (2006.01)
*C12M 1/12* (2006.01)
*C12M 1/04* (2006.01)

(52) U.S. Cl.
CPC ............ *C12M 29/04* (2013.01); *B01J 19/0073* (2013.01); *C12M 23/24* (2013.01); *C12M 23/26* (2013.01); *C12M 23/34* (2013.01); *C12M 23/44* (2013.01); *C12M 23/46* (2013.01); *C12M 25/02* (2013.01); *C12M 29/10* (2013.01); *B01J 2219/00011* (2013.01)

(58) Field of Classification Search
CPC ................... B01J 19/0073; B01J 2219/00011; C12M 23/26; C12M 23/44; C12M 23/24; C12M 23/34; C12M 23/46; C12M 25/02; C12M 29/04
USPC ...................................................... 435/289.1
See application file for complete search history.

(56) References Cited

U.S. PATENT DOCUMENTS

2003/0082632 A1    5/2003   Shumate
2008/0101997 A1    5/2008   Beebe

FOREIGN PATENT DOCUMENTS

EP          1 762 300 A2      3/2007
WO       WO 97/44132 A1     11/1997

OTHER PUBLICATIONS

International Search Report for PCT/GB2009/050965. Aug. 23, 2010.

*Primary Examiner* — Michael Hobbs
(74) *Attorney, Agent, or Firm* — Myers Bigel Sibley & Sajovec, PA

(57) ABSTRACT

Embodiments of the invention provide a chamber for a bioreactor, the chamber having a fluid inlet aperture and a fluid outlet aperture disposed at respective different locations of a wall of the chamber, with respect to a normal upright orientation of the chamber the chamber being provided with an upper wall portion defining an upper boundary of the chamber. The upper wall portion has an internal surface having a first portion that is vertically displaced with respect to a second portion. The internal surface of the upper wall portion is arranged to promote expulsion of trapped gas bubbles through the outlet aperture, the first and second portions of the upper wall portion each comprising a sloped portion.

20 Claims, 15 Drawing Sheets

(a)

(b)

(c)

(d)

BIOREACTOR CHAMBER

RELATED APPLICATIONS

The present application is a 35 U.S.C. §371 national phase application of PCT International Application No. PCT/GB2009/050965 having an international filing date of Jul. 31, 2009, claiming priority to Great Britain Patent Application No. 0814034.5, filed Aug. 1, 2008; Great Britain Patent Application No. 0814033.7, filed Aug. 1, 2008; Great Britain Patent Application No. 0908400.5, filed May 15, 2009; and Great Britain Patent Application No. 0908404.7, filed May 15, 2009. The disclosures of each application are incorporated herein by reference in their entireties. The above PCT International Application was published in the English language as International Publication No. WO 2010/013069 A2.

FIELD OF THE INVENTION

The present invention relates to bioreactors. In particular but not exclusively the present invention relates to a culture chamber for use in a bioreactor.

BACKGROUND

It is known provide a bioreactor having a culture chamber and means for passing a flow of culture medium through the chamber in order to enable a wide range of studies of biological materials. By way of example, the biological material under investigation may be a monolayer cell culture, scaffold culture or tissue slice. WO2005/123258 discloses a bioreactor for studying the effects of imposed stimuli on cellular activity.

A number of problems are associated with known culture chambers. For example known chambers exhibit non-uniform flow patterns that can result in turbulent flow and the formation of bubbles and/or foam within the chamber. Known chambers are also not easy to assemble and disassemble. These factors can lead to problems in successfully seeding and growing cells within the chambers.

An aim of the present invention is to at least partially mitigate at least one of the above mentioned problems.

STATEMENT OF THE INVENTION

In a first aspect of the invention there is provided a chamber for a bioreactor, the chamber having a fluid inlet aperture and a fluid outlet aperture disposed at respective different locations of a wall of the chamber, with respect to a normal upright orientation of the chamber the chamber being provided with an upper wall portion defining an upper boundary of the chamber, the upper wall portion having an internal surface having a first portion that is vertically displaced with respect to a second portion, the internal surface of the upper wall portion being arranged to promote expulsion of trapped gas bubbles through the outlet aperture, the first and second portions of the upper wall portion each comprising a sloped portion.

Reference to trapped gas bubbles includes reference to gas bubbles present in the chamber whether introduced through the inlet aperture or evolved by biological or other reaction within the chamber.

A chamber according to the present invention has the advantage that a disruption in a flow pattern of fluid through the chamber due to the presence of gas bubbles may be reduced.

In some known chambers the extent to which fluid flow through the chamber is laminar is compromised in the presence of gas bubbles. This increases a risk that cell viability or function in the chamber will suffer.

In some embodiments of the invention an increased rate of growth of cells is observed due at least in part to a reduction in the number of bubbles present in the chamber. In some embodiments an increase in cell function and/or viability is obtained.

The first and second portions may comprise a portion curved in cross-section as viewed along a direction normal to an imaginary line drawn from the first portion to the second portion of the upper wall portion.

Preferably the first and second portions comprise a portion defining a portion of a substantially spherical surface.

The upper wall portion may comprise a substantially domed portion.

The upper wall portion may comprise a distorted domed portion having an apex displaced with respect to a geometric apex of a nominally cylindrically symmetrical domed portion.

Preferably the sloped portion is disposed between the inlet and outlet apertures, the slope being in a direction substantially parallel to an imaginary line from the inlet aperture to the outlet aperture.

Preferably the sloped portion is provided such that the first portion of the internal surface is closer to the outlet aperture than the second portion.

Preferably the internal surface of the upper wall is provided with at least a portion defining a channel, thereby to promote flow of trapped gas bubbles through the outlet aperture.

The channel may have a shape as viewed along a direction parallel to an imaginary line drawn from the first portion to the second portion of the upper wall portion that is at least one selected from amongst curved, substantially V-shaped and substantially U-shaped.

This has the advantage that gas bubbles may be expelled from the chamber more effectively without a risk that a gas bubble will become fixed to an internal wall of the chamber.

Preferably the channel has a shape as viewed along a direction parallel to an imaginary line drawn from the first portion to the second portion of the upper wall portion that is substantially V-shaped and an inner angle of the substantially V-shaped channel is from around 90° to around 176°, preferably from around 150° to around 174°, more preferably from around 170° to around 172°.

This feature has the advantage of further increasing a probability that a gas bubble will be expelled from the chamber via the outlet aperture.

The sloped portion of the upper wall may be arranged to slope at an angle of from around 2° to around 30° with respect to a horizontal plane, preferably from around 2° to around 10°, more preferably from around 5° to around 8°, optionally from around 5° to around 7°.

Preferably the outlet aperture is provided at a location of an inner surface of the wall of chamber at or proximate an uppermost portion of the inner surface with respect to a normal upright orientation of the chamber.

This has the advantage of increasing a probability that a gas bubble will be drawn from the chamber and through an outlet aperture.

More preferably the fluid outlet aperture is provided at a location displaced in a vertical direction relative to the fluid inlet aperture.

Preferably a diameter of the outlet aperture is greater than a diameter of the inlet aperture.

The diameter of the outlet aperture may be greater than that of the inlet aperture by at least a factor of 1.5.

Optionally the diameter of the outlet aperture may be greater than that of the inlet aperture by at least a factor of 2.

Preferably the fluid inlet and fluid outlet are provided at substantially opposed locations of the inner wall of the chamber.

Preferably the chamber is substantially cylindrical.

Preferably the inlet aperture and the outlet aperture are provided at diametrically opposite locations of the inner wall of the chamber as viewed along a substantially vertical axis.

Preferably the chamber is further provided with a sample support arranged to support a sample in the form of a membrane, the support being arranged to allow each of a pair of opposed major faces of the membrane to be exposed to fluid contained within the chamber.

The sample support may comprise at least one support member arranged to contact a portion of the sample.

The at least one support member may comprise a ridged element, the ridged element being elongate in a substantially lateral direction thereby to provide an elongate surface upon which a sample may be placed.

The at least one support member may comprise a post element.

Preferably the post element is provided with an upper surface arranged to contact a sample supported by the at least one support member, the upper surface being one selected from amongst substantially flat, substantially curved and substantially domed.

Alternatively or in addition the at least one support member may comprises an element substantially in the form of a hemisphere or portion thereof.

The chamber may comprise a body portion and a basal portion, the sample support being provided in the basal portion, the body portion comprising the upper wall, the basal portion being a portion at an opposite end of the chamber to the upper wall.

The basal portion and body portion may be arranged to be coupled to one another by means of one or more complementary formations.

The basal and body portions may be arranged to be releasably coupled to one another.

Preferably one or more complementary formations of a portion is/are provided by a rim at an end of a wall of the one portion, the rim having a recess formed in a radially inner circumferential region of the rim whereby a radially outer region of the rim defines a substantially circumferential skirt.

It is to be understood that reference to a radially inner circumferential region includes reference to a corresponding 'inner' region of a perimeter of a rim of a portion of a chamber that is not substantially circular, but may instead be substantially in the form of a square or any other suitable geometric shape having substantially any number of flat or substantially curved sides.

The corresponding formation of the other portion of the chamber may be provided by a recess provided in a radially outer circumferential region of a rim of said other portion having a size and shape corresponding to the skirt of said one portion.

The basal portion may be coupled to the body portion by means of a friction-fit.

Preferably at least one of the basal and body portions is formed from a resiliently deformable material.

Preferably at least one of the basal and body portions is formed from a material having a self-adhesive property.

Preferably at least one of the basal and body portions is formed from a silicone material.

Preferably at least one of the basal and body portions is formed from a substantially transparent or translucent material.

Preferably a chamber is further provided with clamping members operable to clamp the portions together thereby to prevent leakage of fluid from the chamber.

Preferably at least a portion of a wall of the chamber comprising a siloxane.

At least a portion of a wall of the chamber may comprise polydimethylsiloxane (PDMS).

In a second aspect of the invention there is provided a bioreactor chamber assembly comprising a chamber according to the first aspect having a body portion and a basal portion;

a pair of clamp members; and a pair of resilient loop elements, wherein the clamp members are arranged to sandwich the chamber between the clamp members and the loop elements are arranged to apply a force between the clamp members to urge the basal and body portions of the chamber towards one another, each loop element being arranged to apply a force to each clamp member at a different respective position of each clamp member such that each loop element applies a substantially equal and opposite torque to each clamp element about an axis normal to a direction along which the force is applied between the clamp members.

Preferably the clamp members are each provided with a recessed portion arranged to receive a portion of the chamber therein.

The clamp members may each comprise a substantially plate-like member.

The clamp members may be provided with one or more grip portions arranged to constrain movement of the loop elements with respect to the clamp members when the loop elements apply said force between the clamp members.

The one or more grip portions may each comprise a grooved portion of a clamp member.

Preferably the grooved portion is provided on a side of a clamp member opposite the side on which the chamber is provided.

Preferably at least one clamp member comprises a substantially disc-shaped member.

The loop elements may each comprise an endless loop.

Optionally a pair of loop elements are provided by a single endless loop. In such an embodiment the single endless loop may be provided in a figure of 8 form. One clamp member may be adapted to accommodate a cross-over of the figure of 8 form.

The loop elements may be formed from an elastomeric material.

One of the clamp members may be fixedly attached to a substrate.

One of the clamp members may be provided by a substrate.

The substrate may provide a clamp member of a plurality of assemblies.

In a third aspect of the invention there is provided a bioreactor chamber assembly comprising: a chamber having a basal portion and a body portion arranged to be coupled to one another; a pair of clamp members; and a pair of resilient loop elements, wherein the clamp members are arranged to sandwich the chamber between the clamp members and the loop elements are arranged to apply a force between the clamp members to urge the basal and body portions of the chamber towards one another, each loop element being arranged to apply a force to each clamp member at a different respective position of each clamp member such that each loop element applies a substantially equal and opposite torque to each clamp element about an axis normal to a direction along which the force is applied between the clamp members.

In a fourth aspect of the invention there is provided a chamber for a bioreactor, the chamber having a fluid inlet aperture and a fluid outlet aperture and a sample support arranged to support a sample in the form of a membrane, the support being arranged to allow each of a pair of opposed major faces of the membrane to be exposed to fluid contained within the chamber.

Preferably the sample support comprises a plurality of mutually spaced apart support members each support member being arranged to contact a portion of the sample.

Preferably the plurality of support members are substantially parallel to one another.

The support members may be of substantially square or rectangular cross-section.

Preferably the chamber comprises a body portion and a basal portion, the sample support being provided in the basal portion, the basal portion being a portion at a lower end of the chamber with respect to a normal upright orientation of the chamber.

Preferably the basal and body portions are arranged to couple to one another at least in part by means of a friction fit.

Preferably at least one of the basal and body portions is formed from a resiliently deformable material.

Preferably at least one of the basal and body portions is formed from a material having a self-adhesive property.

At least one of the basal and body portions may be formed from a silicone material.

Preferably at least one of the basal and body portions is formed from a substantially transparent or translucent material.

The chamber may be further provided with clamping members operable to clamp the portions together thereby to prevent leakage of fluid from the chamber.

In one aspect of the invention there is provided a chamber for a bioreactor, the chamber having a fluid inlet aperture and a fluid outlet aperture disposed at respective different locations of a wall of the chamber, with respect to a normal upright orientation of the chamber the fluid outlet aperture being provided at a location displaced in a vertical direction relative to the fluid inlet aperture, the chamber being provided with an upper wall defining an upper boundary of the chamber, the upper wall having a sloped portion having an internal surface having an upper region vertically displaced with respect to a lower region and arranged to promote expulsion of trapped gas bubbles through the outlet aperture.

BRIEF DESCRIPTION OF THE DRAWINGS

Embodiments of the invention will now be described with reference to the accompanying figures in which.

DETAILED DESCRIPTION

Figure 1:
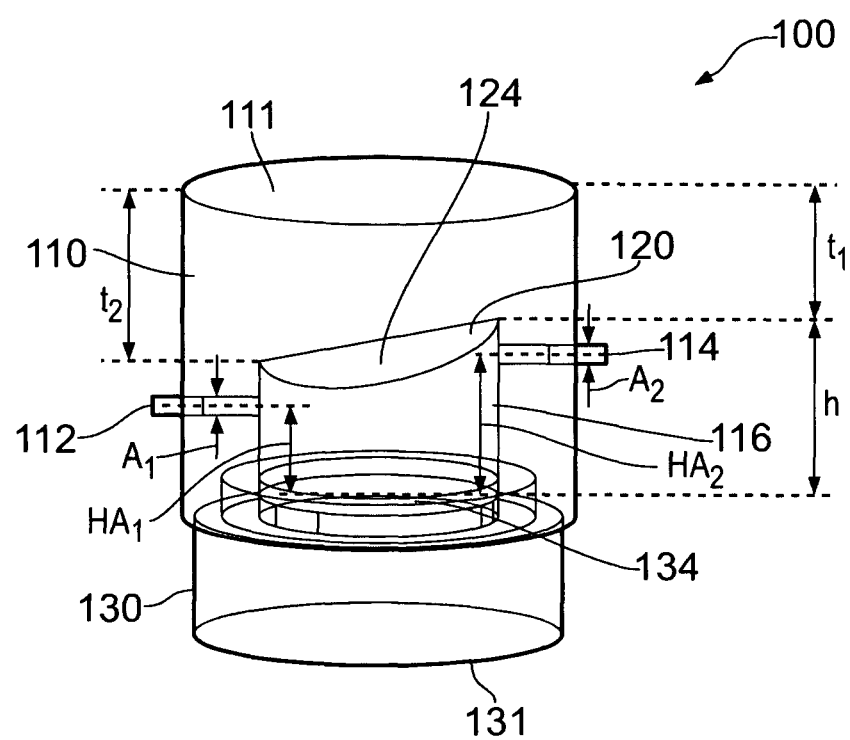
FIG. 1 shows a culture chamber according to an embodiment of the invention.

In one embodiment of the invention a chamber 100 which may be used as a culture chamber is provided as shown in FIG. 1. The chamber 100 has a body portion 110 and a basal portion 130. The chamber 100 is arranged to be supported in normal use by resting of the basal portion 130 on a substantially horizontal surface in the orientation shown in FIG. 1.

The body portion 110 has an internal cavity 116 in fluid communication with a fluid inlet aperture 112 and a fluid outlet aperture 114. In the orientation shown in FIG. 1 the inlet aperture 112 and outlet aperture 114 are provided at diametrically opposed locations of the chamber 100, the outlet aperture 114 being arranged to be at a greater height above the basal portion 130 than the inlet aperture 112.

Figure 2:
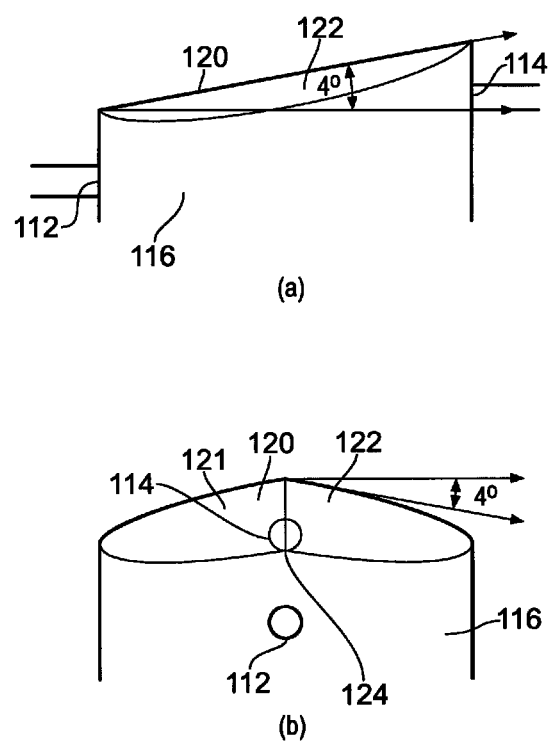
FIG. 2 shows detail in respect of (a) a slope of an upper surface of the chamber and (b) a pitch of walls of a channel region formed in the upper surface of the chamber.

An upper internal surface 120 of the body portion 110 is shaped to provide a shallow substantially V-shaped channel 124 (FIG. 2(b)) defined by internal surfaces 121, 122 that are provided at an angle of substantially 172° to one another. In the normal upright orientation of FIG. 1 the channel 124 slopes in an upward direction from the fluid inlet aperture 112 to the fluid outlet aperture 114 at angle of substantially 7°.

The channel 124 is arranged to promote expulsion of gas bubbles from the internal cavity 116 through the outlet aperture 114. The presence of gas bubbles can have a deleterious effect on the function of biological material in the culture chamber since it can have the effect of modifying the laminarity and vorticity of the flow of fluid such as culture medium through the chamber 100. This can result in a change in a flow pattern of fluid over a sample provided on a sample support 134.

In the chamber 100 of FIG. 1 the diameter of the internal cavity 116 is around 15 mm and the total height h of the cavity is around 13 mm at the highest point of the cavity 116. A cylindrical wall of the cavity is around 6 mm thick, an upper wall of the cavity having a thickness tapering from a thickness of around $t_1$ to a thickness of around $t_2$, from a portion proximate the outlet aperture to a portion proximate the inlet aperture. In some embodiments thickness $t_1$ is around 1 mm and thickness $t_2$ is around 3 mm.

The inlet aperture has a diameter $A_1$ of around 1 mm and the outlet aperture has a diameter $A_2$ of around 2 mm. A longitudinal axis of the inlet aperture is located a distance $HA_1$ above the basal portion, being around 9 mm in the embodiment of FIG. 1. A corresponding axis of the outlet aperture is located a distance $HA_2$ above the basal portion, distance $HA_2$ being around 10.5 mm. Thus the outlet aperture is displaced in a vertical direction with respect to the inlet aperture by a distance of around 1.5 mm.

In some embodiments the inlet aperture 112 has a smaller diameter than that of the outlet aperture 114 in order to improve the extent to which flow of fluid over the sample surface is laminar and not turbulent. As fluid enters the chamber 100 through the inlet aperture 112 development of the flow occurs since the direction of fluid flow is no longer restricted to a direction parallel to an axis of the inlet pipe. It is to be understood that by providing an outlet aperture 114 with a larger diameter than the inlet aperture 112 an amount of fluid passing through the fluid inlet aperture 112 that is deflected by a wall of the chamber on an opposite side of the chamber to the fluid inlet aperture 112 may be reduced. This in turn reduces an amount of turbulence generated by a flow of fluid from the inlet aperture 112 to the outlet aperture 114.

Experiments by the present inventors indicate that cells on a sample surface may be deleteriously affected by shear stress imposed on the surface by fluid flowing over the surface. The greater the distance of the inlet and outlet apertures 112, 114 from the sample surface, the lower the amount of shear stress imposed on the sample surface.

However, it is also important to maintain laminar flow over the sample surface in order to avoid turbulent flow since turbulent flow can also have a deleterious effect on cells. The smaller the distance of the inlet and outlet apertures 112, 114 from the sample surface the greater the extent to which fluid flow over the sample surface will be laminar. Furthermore, in some circumstances an extent to which oxygen depletion occurs at the sample surface is reduced as the distance of the inlet and outlet apertures 112, 114 from the sample surface is reduced.

Thus it is to be understood that a distance of each of the inlet and outlet apertures 112, 114 above the sample surface may be selected to provide optimum conditions for the cells.

Figure 3A:
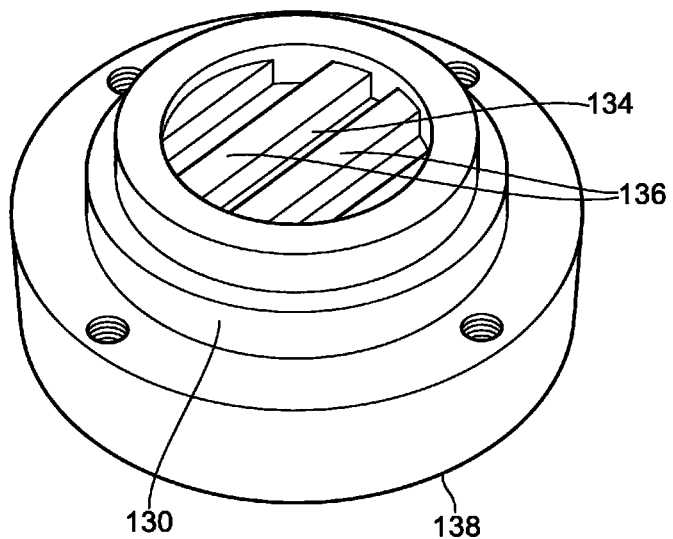
FIG. 3 shows a basal portion of the chamber.
Figure 3:
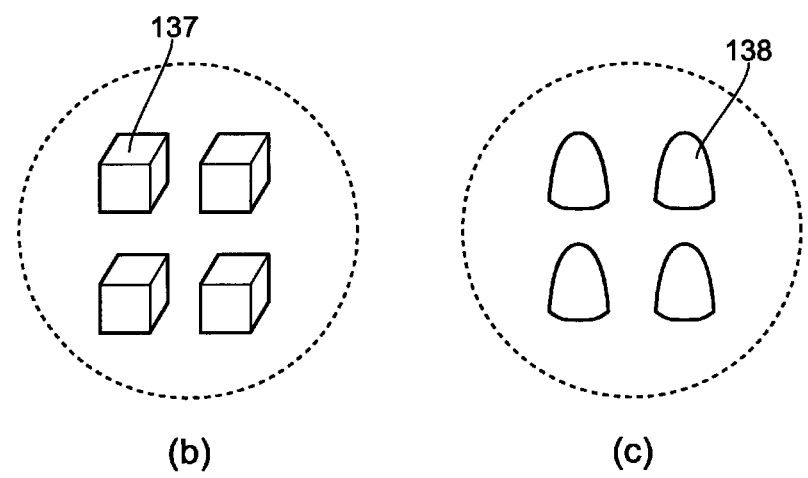

As can be seen in FIG. 3 (a), the basal portion of the chamber 100 has a sample support portion 134 having a plurality of spaced apart ridge elements 136. The ridge elements 136 are arranged to support the sample in such a manner that fluid within the internal cavity 116 of the chamber 200 is able to contact exposed portions of the sample on a face of the sample that is towards the sample support portion 134 as well as a face of the sample that is away from the sample support portion 134. This feature reduces a risk that a tissue sample will experience necrosis on the face that is towards the sample support portion.

It will be apparent to persons skilled in the art that the chamber may be formed by moulding. Other methods of forming the chamber are also useful.

Whilst the embodiment of FIG. 3(a) is provided with ridge elements, it is to be understood that in some other embodiments one or more post elements may be provided. FIG. 3(b) shows an embodiment in which post elements are provided in the form of rectangular cuboids 137 whilst FIG. 3(c) shows an embodiment in which post elements are provided in the form of domed elements 138. Other shapes are also useful. In some embodiments one or more domed formations may be provided.

In FIG. 3(a) the basal portion 130 is shown mounted on a lower clamp (or flange) member 138. The lower clamp member is formed from a stainless steel material and is arranged to cooperate with an upper clamp member (not shown) to prevent the body portion 110 and basal portion 130 from separating, or fluid leaking from between the portions 110, 130 when fluid is passed through the chamber. The chamber is essentially sandwiched between the upper and lower clamp members and the clamp members held together by bolt or clamp members. Other means for holding the clamp members together are also useful.

In the embodiments shown the basal and body portions 130, 110 are arranged to couple to one another at least in part by means of a friction fit, allowing the portions to be releasably coupled to one another in a convenient manner not requiring special tools. Both the basal and body portions are formed from a silicone rubber material, being a resiliently deformable material having a self-adhesive property. This promotes the formation of a substantially water-tight joint between the portions 110, 130.

In the embodiment shown the silicone rubber is formed to be substantially transparent to light, allowing cells within the chamber 100 to be exposed to light to test an influence of visible (or infra-red) light on cell function and/or viability. In some embodiments the silicone rubber is formed to be substantially opaque.

It is to be understood that other materials and forms of material are also useful.

Figure 4:
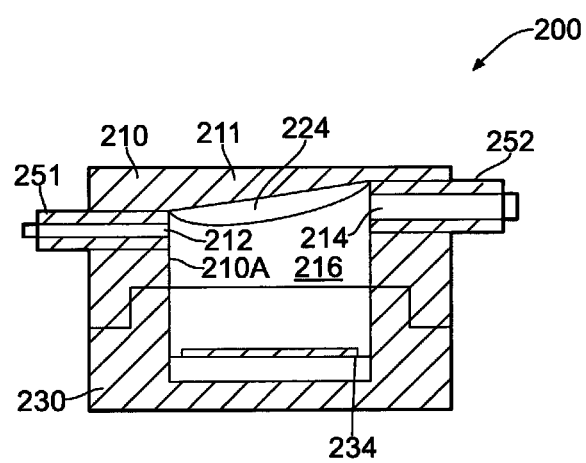
FIG. 4 shows a cross-sectional view of a chamber according to an embodiment of the invention.

FIG. 4 shows a chamber 200 having a body portion 210 and a basal portion 230 similar to the embodiment of FIG. 1. The body portion 210 has an inner internal cavity 216 having a diameter of 15 mm.

An inlet tube 251 is coupled to the chamber to provide a flow of fluid through an inlet aperture 212 of the chamber. The inlet tube 251 has an outer diameter of 3 mm and an inner diameter of 1 mm. Other diameters are also useful.

The inlet tube 251 provides the inlet aperture 212 at a distance of around 1 mm below an intersection of an upper inner wall 224 of the chamber 200 with an inner side of a sidewall 210A of the chamber 200, proximate a lowest point of the upper inner wall 224 with respect to a normal upright orientation of the chamber 200.

A sample support portion 234 is provided by the body portion, the sample support portion providing a surface for supporting a sample that is located a distance of 8 mm below a lower edge of the inlet tube 251 as show in FIG. 4. Other distances are also useful.

A corresponding outlet tube 252 is provided diametrically opposite the inlet tube 251. The outlet tube has an outer diameter of 4 mm and an inner diameter of 2 mm. A lower edge of the outlet tube 252 is provided a distance 9 mm above the sample support portion 234. The outlet tube 252 provides the outlet aperture 214 of the chamber 200.

As in the case of the embodiment of FIG. 1 the thickness of an upper wall 211 of the chamber is around 1 mm at a location proximate the outlet aperture and around 3 mm at a location proximate the inlet aperture. Thus, a slope of a channel 224 between the inlet and outlet apertures is around 7-8°. Other angles are also useful.

Figure 5:
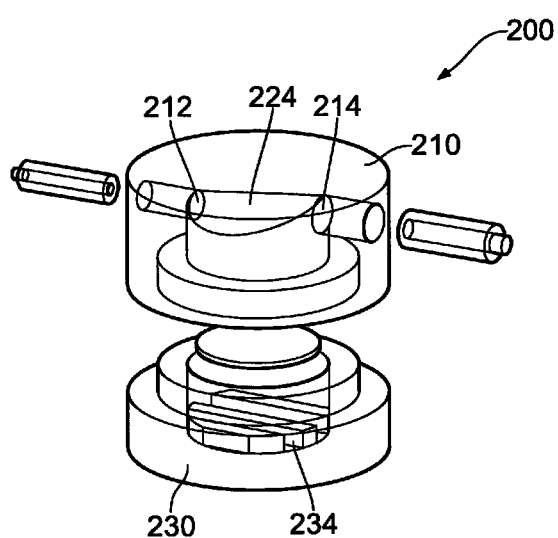
FIG. 5 shows a perspective exploded view of the embodiment of FIG. 4.

FIG. 5 is an exploded view of the chamber 200 of FIG. 4.

Figure 6:
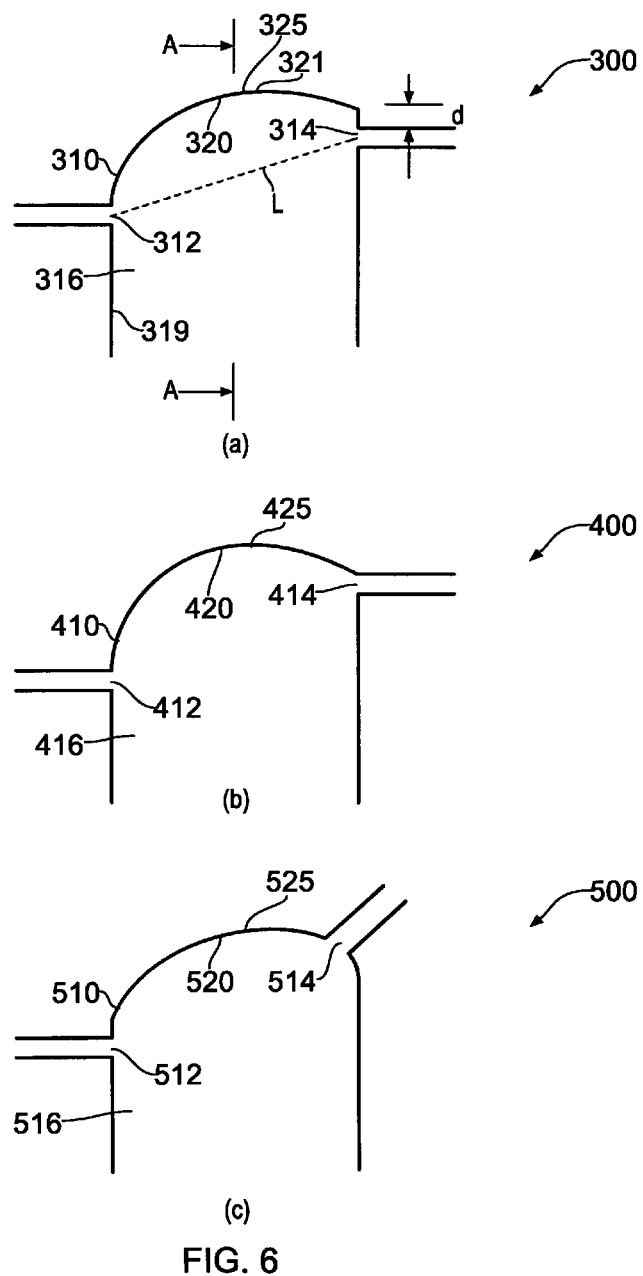
FIG. 6 (a) to (d) shows a series of embodiments of the invention in which an upper internal surface of a chamber is curved as viewed in cross-section.
Figure 6:
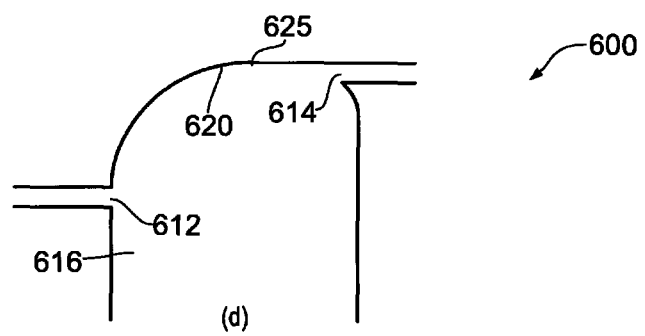

FIG. 6 shows a series of embodiments of the invention in which an internal surface of an upper wall of a body portion of a chamber has a substantially domed shape.

FIG. 6(a) shows a chamber 300 having a body portion 310. The body portion has an internal cavity 316 having a wall having an upper internal surface 320. A fluid inlet aperture 312 and a fluid outlet aperture 314 allow a fluid to be passed through the internal cavity 316.

In the embodiment of FIG. 6(a) the upper internal surface 320 of the body portion 310 of the chamber 300 is curved as viewed along a direction normal to an imaginary line L drawn from the fluid inlet 312 to the fluid outlet 314. In some embodiments the upper internal surface 320 is substantially in the form of a portion of a sphere. Other shapes are also useful.

In the embodiment of FIG. 6(a) a portion 319 of an internal surface of the body portion 310 below the upper internal surface 320 is substantially cylindrical. In the embodiment of FIG. 6(a) the outlet aperture 314 is displaced below an upper boundary of the cylindrical portion of the body portion 310 by a distance d. d may be around 1 mm. Other distances are also useful.

The embodiment of FIG. 6(b) is similar to that of the embodiment of FIG. 6(a) and like reference numerals are used to indicate corresponding features. However in the embodiment of FIG. 6(b) the distance corresponding to distance d shown in FIG. 6(a) is substantially zero.

The embodiment of FIG. 6(c) is similar to that of the embodiments of FIG. 6(a) and (b) and like reference numerals are used to indicate corresponding features. However in the embodiment of FIG. 6(c) the outlet aperture 514 is provided in the upper internal surface 520 which is curved. In some embodiments the outlet aperture 514 is provided downstream of an apex 525 of the domed portion. By apex 525 is meant a region or point of the upper internal surface 520 that is uppermost with respect to the normal upright orientation of the chamber 500 shown in FIG. 6(c).

The embodiment of FIG. 6(d) is similar to that of the embodiment of FIG. 6(c) except that an outlet aperture 614 is provided at or proximate the apex of the internal surface 620 of the chamber 600.

Figure 7:
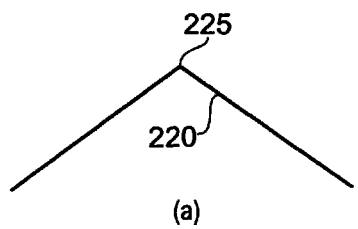
FIG. 7 shows a series of embodiment of the invention in which a channel provided in an upper internal surface of the chamber is (a) substantially V-shaped, (b) substantially a rounded V-shape, (c) curved and (d) substantially U-shaped.
Figure 7:
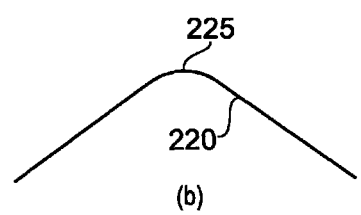
Figure 7:
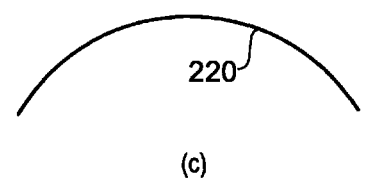
Figure 7:
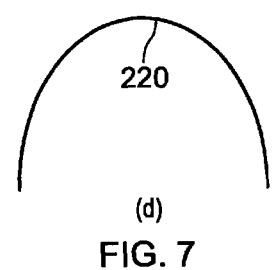

FIG. 7 shows a cross-sectional view of the upper internal surface 220 of a chamber as viewed along a direction substantially parallel to an imaginary line L from the inlet aperture to the outlet aperture (in a similar manner to line L of FIG. 6(a)).

The embodiment of FIG. 7(a) has a substantially V-shaped internal surface 220 having an angular apex 225 whilst the embodiment of FIG. 7(b) has a substantially V-shaped internal surface with a rounded apex 225.

The embodiment of FIG. 7(c) has a substantially curved internal surface 220 whilst the embodiment of FIG. 7(d) has a substantially U-shaped internal surface 220.

It is to be understood that in some embodiments an outer surface 111 of the upper portion of the body portion 110 (see e.g. FIG. 1) may be substantially flat. The outer surface 111 of the upper portion of the body portion 110 may also be arranged to be substantially parallel to an outer surface 131 of a lower portion of the basal portion 130.

Both the outer surface 111 of the upper portion of the body portion 110 and the outer surface 131 of the lower portion of the basal portion 130 (FIG. 1) may be arranged to lie in a substantially horizontal plane when the chamber is in a normal upright orientation.

This feature has the advantage that in some embodiments clamping of the body portion 110 to the basal portion 130 may be facilitated more readily.

For example, as described above the basal portion 130 of the chamber of FIG. 3 is shown mounted on a lower clamp member 138. The lower clamp member 138 may be coupled to an upper clamp member not shown in FIG. 1.

Figure 8A:
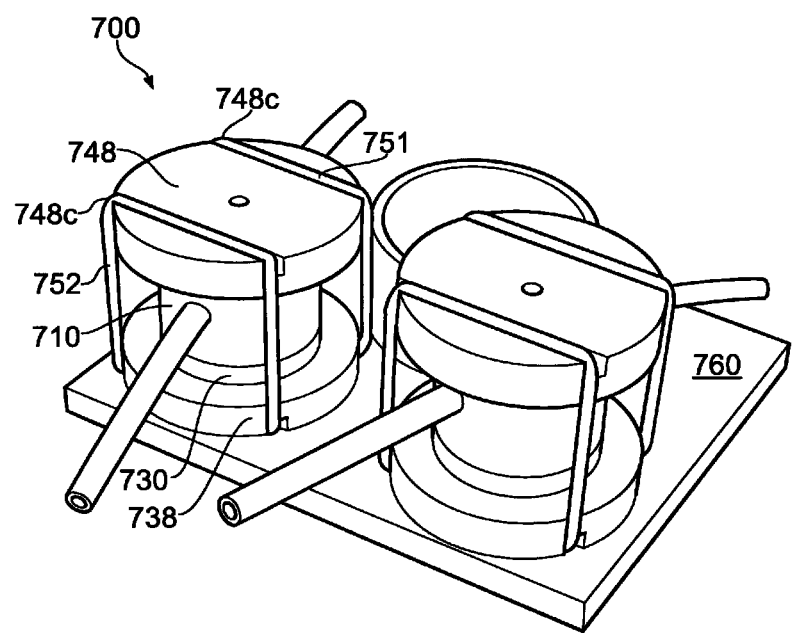
FIG. 8 shows a chamber assembly according to an embodiment of the invention in which a chamber is sandwiched between two clamp members.
Figure 8B:
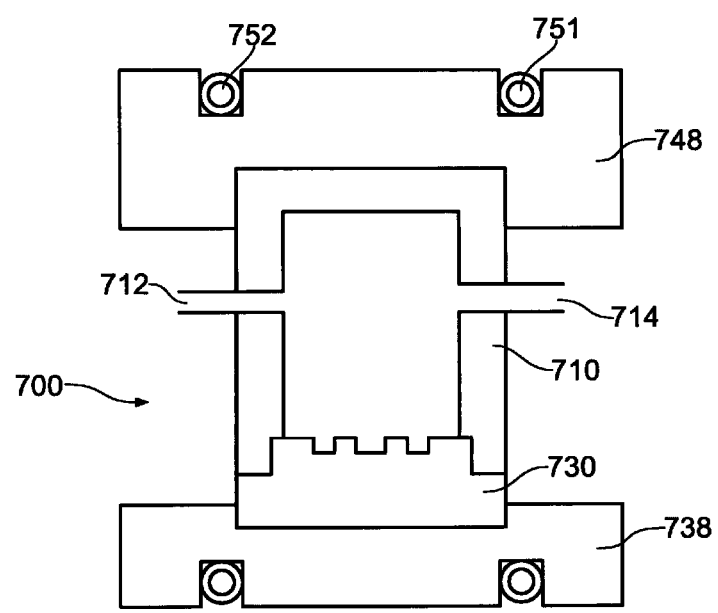

FIG. 8(a) shows an embodiment of the invention having a pair of clamp members 738, 748 arranged to sandwich a basal portion 730 and a body portion 710 of a chamber 700 therebetween. FIG. 8(b) shows a corresponding cross-sectional view of the clamp members 738, 748 and chamber 700. It can be seen that the chamber 700 has an inlet aperture 712 and an outlet aperture 714.

Figure 9A:
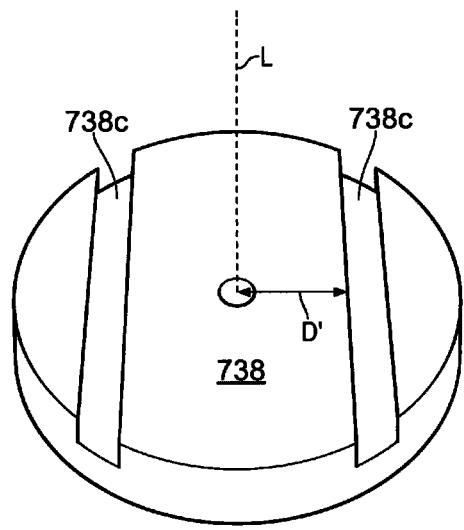
FIG. 9 shows (a) an outer surface and (b) an inner surface of a clamp member according to an embodiment of the invention.
Figure 9B:
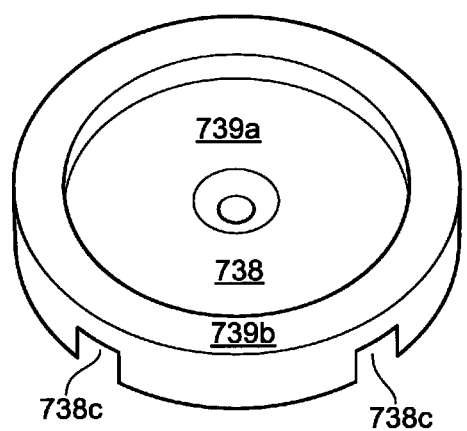

In some embodiments the clamp members 738, 748 are substantially identical. As can be seen from FIG. 8 and FIG. 9 the clamp members 738, 748 are in the form of disc-like members each having a side having a recessed well portion 739a and a corresponding rim portion 739b (FIG. 9(a)). The well portion 739a of one clamp member 738 is sized to receive a portion of the basal portion 730 of the chamber therein.

The other clamp member 748 has a corresponding recessed well portion arranged to receive a portion of the body portion 710 therein.

Thus in some embodiments the chamber 700 is arranged to be locatable between the clamp members 738, 748 whereby lateral movement of the clamp members with respect to the chamber 700 is constrained by the presence of the rim portions 739b.

In order to provide a clamping force between the clamp members 738, 748, in the embodiment of FIGS. 8 to 11 a pair of resilient elements are provided in the form of endless loops 751, 752. The clamp members 738, 748 are provided with recessed channels 738c on an outer major surface thereof (being the surface opposite the surface in which the well portion 739a is provided). In the embodiment shown the recessed channels 738c are substantially parallel to one another and are provided at locations disposed equal distances D' from a longitudinal axis L of the disc element 738, 748 but on opposite sides of the axis L. Thus, distance D' is a radial distance of the closest point of channel 738c to the axis L. In some embodiments where the clamp member 738 is a disc-like member distance D' is around two thirds of a radius of the clamp member 738. Other distances are also useful.

Figure 10:
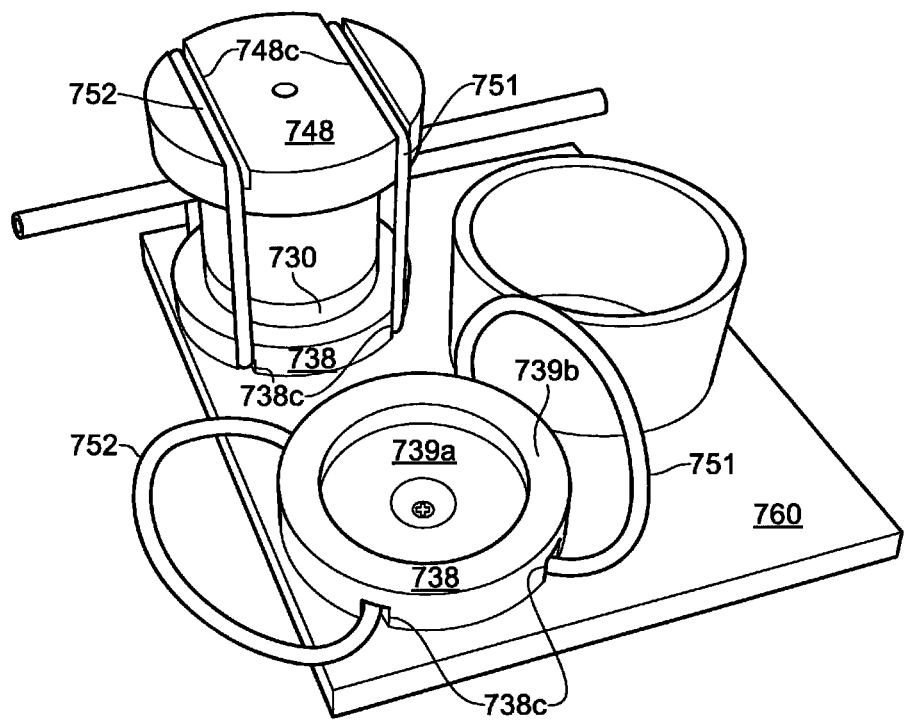
FIG. 10 is a perspective view of a substrate having a pair of clamp members fixedly coupled thereto to which respective chambers may be attached.
Figure 11:
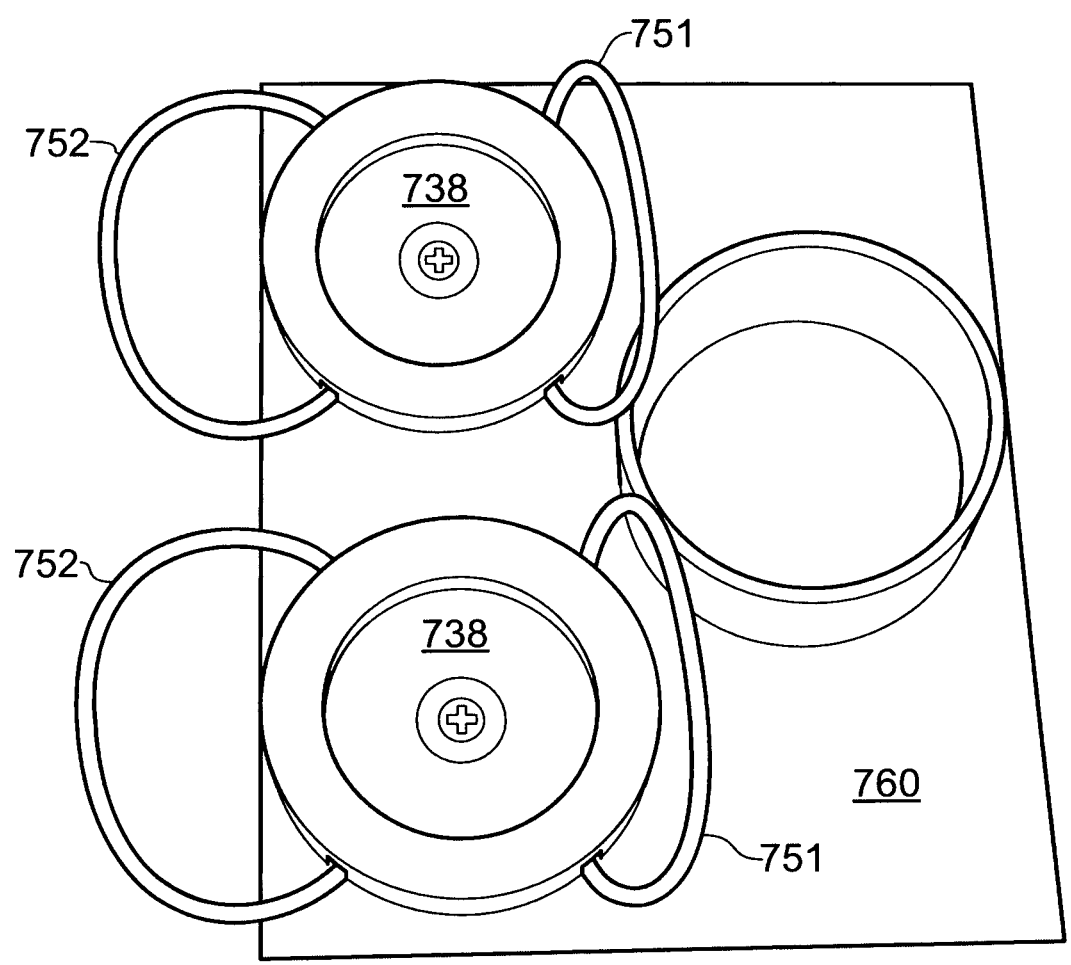
FIG. 11 is a plan view of the embodiment of FIG. 10

In the embodiment of FIGS. 10 and 11 a lower clamp member 738 is coupled to a substrate 760 trapping the loops 751, 752 to lie within their respective channel 738c. The lower clamp member 738 may be coupled to the substrate 760 by permanent fixing means such as an adhesive or by means of releasable fixing means. The releasable fixing means may be a mechanical fixing element such as a screw or bolt, hook and loop fixing means (e.g. Velcro(R)), a releasable adhesive or any other suitable releasable fixing means.

It can be seen from FIG. 10 that a clamp member 748 (an upper clamp member) is positioned over the chamber with channels 748c of the upper clamp member 748 substantially parallel to those of the lower clamp member 738. The endless loops 751, 752 are sized such that they can be positioned so as to lie in respective channels 748c of the upper clamp member 748. The endless loops are arranged to exert a sufficient force to clamp the body portion 710 and basal portion 730 of the chamber 700 together to prevent leakage of fluid from the chamber through a joint between the body and basal portions 710, 730.

Embodiments such as that of FIGS. 8 to 11 have the advantage that a substantially equal clamping force may be applied by respective resilient elements 751, 752 at substantially equal distances either side of the longitudinal axis L of the chamber 700. Thus, clamping forces applied to the chamber 700 are balanced and a stable clamping arrangement may be provided.

It is to be understood that this has the effect that a torque applied to a clamping member 738, 748 by one resilient element 751, 752 is arranged to act in an opposite direction and to be of substantially equal magnitude to a torque applied by the other resilient element 751, 752. Thus a twisting force on the respective clamp members 738, 748 is substantially zero. This has the advantage discussed above that a stability of the assembly is enhanced.

Furthermore a chamber 700 clamped between clamp members 738, 748 is subject to substantially uniform pressure by the clamp members 738, 748. This has the advantage that a seal between the body portion 710 and basal portion 730 is also subject to uniform pressure by the clamp members 738, 748 reducing a risk of leakage of fluid.

In some embodiments, resilient elements other than endless loops are provided. In some embodiments the resilient elements are in the form of resiliently extensible linear elements. The linear elements may be flexible elements, such as lengths of an elastomer. The linear elements may be provided with one or more hook elements to facilitate coupling of the linear elements to a clamp member.

It is to be understood that in some embodiments the lower and upper clamp members 738, 748 may be formed integrally with basal and body portions of the chamber. Alternatively the lower and upper clamp members 738, 748 may be permanently coupled to basal and body portions of the chamber. In some embodiments the lower and upper clamp members 738, 748 are releasably coupled to basal and body portions of the chamber.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

The invention claimed is:

1. A chamber for a bioreactor, the chamber comprising:
a body portion and a basal portion defining an external surface and an internal surface of the chamber, the internal surface providing a cavity;
a fluid inlet aperture and a fluid outlet aperture disposed at respective different locations of a sidewall of the cavity, with respect to a normal upright orientation of the chamber, the chamber being provided with an upper wall portion defining an upper boundary of the cavity at an opposite end of the chamber from the basal portion, the upper wall portion having an internal surface having a first portion that is vertically displaced with respect to a second portion, the internal surface of the upper wall portion being arranged to promote expulsion of trapped gas bubbles through the outlet aperture, the first and second portions of the upper wall portion each comprising a sloped portion;
an inlet tube coupled to the fluid inlet aperture and an outlet tube coupled to the fluid outlet aperture within the external surface of the chamber;
wherein the fluid inlet aperture and the fluid outlet aperture are provided at substantially opposed locations of the internal surface of the sidewall of the chamber, wherein the fluid inlet aperture and the fluid outlet aperture in the sidewall of the chamber are located in the upper portion of the cavity, and
wherein the inlet tube and the outlet tube extend substantially parallel along their lengths within the external surface of the chamber.

2. A chamber as claimed in claim 1 wherein the first and second portions comprise a portion curved in cross-section as viewed along a direction normal to an imaginary line drawn from the first portion to the second portion of the upper wall portion.

3. A chamber as claimed in claim 1 wherein the sloped portion is disposed between the inlet and outlet apertures, the slope being in a direction substantially parallel to an imaginary line from the inlet aperture to the outlet aperture.

4. A chamber as claimed in claim 1 wherein the internal surface of the upper wall is provided with at least a portion defining a channel configured to promote flow of trapped gas bubbles through the outlet aperture.

5. A chamber as claimed in claim 1 wherein a diameter of the outlet aperture is greater than a diameter of the inlet aperture.

6. A chamber as claimed in claim 5 wherein a diameter of the outlet aperture is greater than a diameter of the inlet aperture by at least a factor of 1.5.

7. A chamber as claimed in claim 1 wherein the chamber is substantially cylindrical.

8. A chamber as claimed in claim 1 further comprising a sample support arranged to support a sample in the form of a membrane, the support being arranged to allow each of a pair of opposed major faces of the membrane to be exposed to fluid contained within the chamber.

9. A chamber as claimed in claim 8 wherein the sample support comprises at least one support member arranged to contact a portion of the sample.

10. A chamber as claimed in claim 1 wherein the sample support is provided in the basal portion, the body portion comprising the upper wall, the basal portion being a portion at an opposite end of the chamber to the upper wall.

11. A chamber as claimed in claim 10 wherein the basal portion and body portion are arranged to be coupled to one another by one or more complementary formations.

12. A chamber as claimed in claim 11 wherein the basal and body portions are arranged to be releasably coupled to one another.

13. A chamber as claimed in claim 11 wherein the one or more complementary formations of one portion is/are provided by a rim at an end of a sidewall of the one portion, the rim having a recess formed in a radially inner circumferential region of the rim wherein a radially outer region of the rim defines a substantially circumferential skirt.

14. A chamber as claimed in claim 13 wherein the corresponding formation of the other portion of the chamber is provided by a recess provided in a radially outer circumferential region of a rim of said other portion having a size and shape corresponding to the skirt of said one portion.

15. A chamber as claimed in claim 10 wherein the basal portion is configured to be coupled to the body portion by a friction-fit.

16. A chamber as claimed in claim 10 wherein at least one of the basal and body portions is formed from a resiliently deformable material.

17. A chamber as claimed in claim 10 wherein at least one of the basal and body portions is formed from a silicone material.

18. A chamber as claimed in claim 10 wherein at least one of the basal and body portions is formed from a substantially transparent or translucent material.

19. A chamber as claimed in claim 1, wherein at least a portion of a wall of the chamber comprises a siloxane.

20. A chamber as claimed in claim 1, wherein the chamber comprises a lower wall portion opposite the upper wall portion, wherein the inlet and the outlet tube are parallel to the lower wall portion along their lengths within the external surface of the chamber.

* * * * *